United States Patent [19]

Nasraoui et al.

[11] Patent Number: 5,223,492
[45] Date of Patent: Jun. 29, 1993

[54] DERIVATIVES OF 19-NOR PROGESTERONE; PROCESS FOR PRODUCING THEM AND THE PHARMACEUTICAL COMPOSITIONS INCORPORATING THEM

[76] Inventors: Nejib M. Nasraoui, 103, avenue H.-Dunant, Bat. 10; Alain Piasco, 19, avenue Frederic-Mistral, both of F-06100 Nice, France

[21] Appl. No.: 749,925

[22] Filed: Aug. 26, 1991

Related U.S. Application Data

[62] Division of Ser. No. 381,742, Sep. 5, 1989, abandoned.

[30] Foreign Application Priority Data

Oct. 27, 1987 [FR] France ................. 87 14806

[51] Int. Cl.⁵ ............. C07J 5/00; C07J 17/00; A61K 31/575; A61K 31/58
[52] U.S. Cl. ................. 514/172; 514/177; 540/114; 552/553
[58] Field of Search ............ 514/172, 177; 540/114; 552/553

[56] References Cited

U.S. PATENT DOCUMENTS

| | | | |
|---|---|---|---|
| 3,018,295 | 1/1962 | Berg et al. | 514/178 |
| 4,544,555 | 10/1985 | Gastaud | 514/177 |
| 4,720,357 | 1/1988 | Tchernatinsky | 514/177 |

FOREIGN PATENT DOCUMENTS 2077877 5/1971 France ................. 552/553

OTHER PUBLICATIONS

Krubineir, et al., J. Org. Chem. vol. 33 (5) 1968 pp. 1715–1718.
March Advanced Organic Chemistry 2nd Ed. [New York, McGraw-Hill Book, 1979] pp. 864–872.
Cooley, et al., Chemical Abstracts, vol. 63, 1965 Abstract 116502-h.

*Primary Examiner*—Mukund J. Shah
*Assistant Examiner*—E. C. Ward
*Attorney, Agent, or Firm*—Gifford, Groh, Sprinkle, Patmore and Anderson

[57] ABSTRACT

This invention relates to the field of chemistry and more precisely to the field of medicinal Chemistry.

It has specifically as subject matter the compounds of general formula I

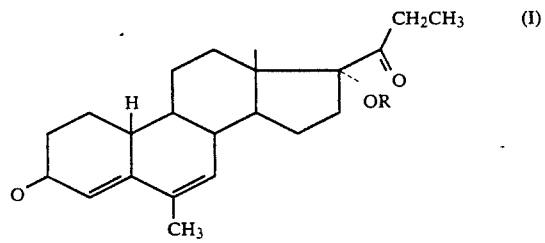

wherein
R is a hydrogen, a lower alkyl radical a methoxymethyl, a tetrahydropyranyl or the acyl residue of an organic carboxylic.

8 Claims, No Drawings

DERIVATIVES OF 19-NOR PROGESTERONE; PROCESS FOR PRODUCING THEM AND THE PHARMACEUTICAL COMPOSITIONS INCORPORATING THEM

This is a divisional of copending application Ser. No. 07/381,742 filed on Sep. 5, 989, now abandoned.

This invention relates to novel derivatives of 18-nor progesterone having the side-chain beared by the carbon 17, including three carbon atoms.

More precisely it has as subject matter derivatives of 19-nor progesterone having on the steroid .. in position 6 a methyl group, on the carbon in 17 position a free, etherified or esterified hydroxyl group and the hydrocarbon side-chain in 17$\beta$- is a propanone-3 chain.

Specifically it has a subject matter the novel derivatives of 19-nor progesterone having the general formula I

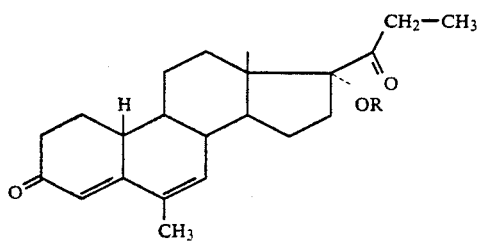

wherein R is a hydrogen, a lower alkyl radical, a methoxymethyl radical, a tetrahydropyranyl radical or the acyl residue of an organic carboxylic or carbonic acid, aliphatic or aromatic, having from 1 to 10 carbon atoms.

In particular this invention relates to the following compounds which are presently the preferred ones:

17$\alpha$-hydroxy 6, 21-dimethyl 3,20-dioxo 19-nor pregna 4,6-diene

17$\alpha$-acetoxy 6,21-dimethyl 3,20-dioxo 19-nor pregna 4,6-diene

17$\alpha$-butyryloxy 6,21-dimethyl 3,20-dioxo 19-nor pregna 4,6-diene

17$\alpha$-tetrahydropyranyloxy 6,21-dimethyl 3,20-dioxo 19-nor pregna 4,6-diene 17$\alpha$-caproyloxy 6,21-dimethyl 3,20-dioxo 19-nor pregna 4,6-diene 17$\alpha$-heptanoyloxy 6,21-dimethyl 3,20-dioxo 19-nor pregna 4,6-diene.

They were already disclosed derivatives of 19-nor progesterone having a methyl substituent in position 6 such as Nomegestrol which is a strong progestative agent endowed with pure progesteronic properties.

They where already known derivatives of 19-nor progesterone the side chain of which in position 17 included 3 carbon atoms and namely 3,20-dioxo 17$\alpha$, 21-dimethyl 19-nor pregna 4,9-diene disclosed in French patent 2.077.877. This kind of compounds shown only mild progestomimetic properties in comparison with their lower homologs.

It has now been found that the compound of general formula I show very interesting progestomimetic properties, mainly through oral way and that their strong binding to the receptors of progesterone implies a strong progestative activity.

The efficiency of these new compounds may be attributed to the steroidal ring structure bearing two bulky substituents, a methyl in position 6 and a methyl in position 21 which without altering the ability to bind on the receptor sites, impedes or refrain the metabolization of the compound in the body through the reducing or hydrogenating enzymes.

In formula I the substituent R may be a lower alkyl radical such as for example a methyl, an ethyl, or an isopropyl. It may also be an acyl residue from an alkyl, or an aryl carboxylic acid such as for example the acetyl residue, the propionyl residue, the butyryl residue, the peutanoyl residue, the hexanoyl residue, the benzoyl radical or the naphtoyl radical. It may further be derivated from an unsaturated acid such as crotonic, senecoioic, or 2-methyl pentenoic acids, or cycloalkyl carbonic acid such as cyclohexyl, or cyclopentyl carbonic acid.

This invention also relates to a process for producing the compounds of formula I which essentially consists in submiting a 17-keto 18-methyl gonadien selected from the group consisting of the 3-alkoxy estra 1,3,5-Trienes of general formula II$_a$

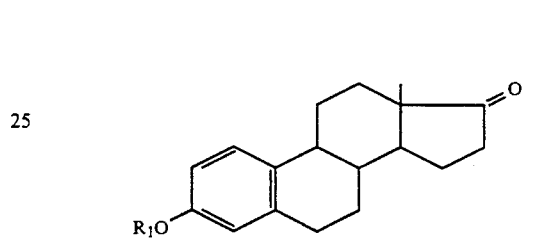

wherein R$_1$ is a lower alkyl radical having from 1 to 6 carbon atoms and the 3-alkoxy estra 3,5-diens of general formula II$_b$

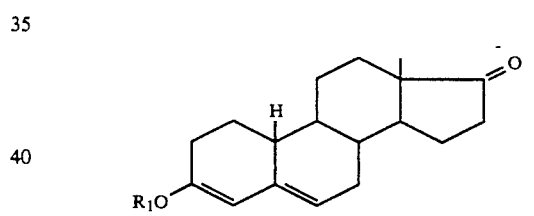

wherein R is defined as previously given to the action of a (triaryl propyl)phosphonium halide or the ylide thereof having the general formulas:

for the phosphonium halide

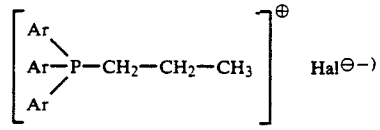

for the corresponding ylide

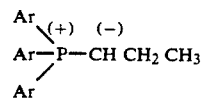

wherein Ar is an unsubstituted or substituted phenyl radical and Hal is a halogen other than fluorine to produce a propylidenic derivative selected from the group consisting of the estra 1,3,5-diene derivatives of general formula III$_a$

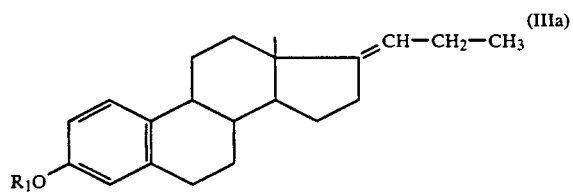

(in the form of a E or Z isomer)
    wherein $R_1$ is defined as previously given and
the estra 3,5-diene derivatives of general formula $III_b$

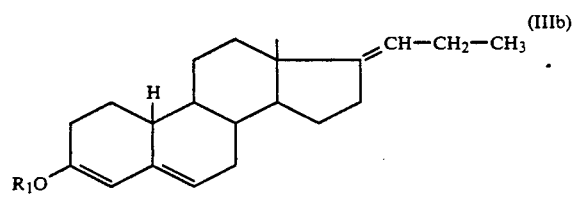

(in the form of a E or Z isomer)
    wherein $R_1$ is defined as previously given.
    submits the compounds of general formula $III_a$ to a hydrogenation according to the Birch's Method to produce a 3-oxo estra 4-en which is converted into a compound of general formula $III_b$ by reacting it with an alkylating agent in acidic medium reacting the said compound of general formula $III_b$ with a formulating agent of the Vilsmeier-Hack type, to produce the corresponding 6-formylated derivative having the general formula IV

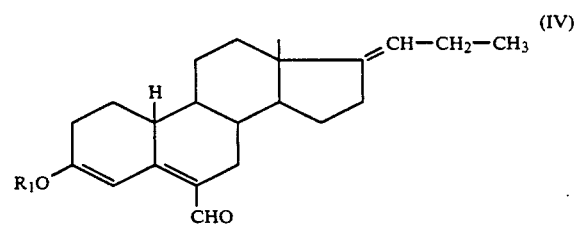

(in the form of a E or Z isomer)
    wherein $R_1$ is defined as previously given one reduces the 6-formylated derivative by means of a mixed alkali metal hydride then one dehydrates the so-formed 6-hydroxy methylated derivative, in acidic medium to produce a 3-oxo 6-methylenic derivative of formula V

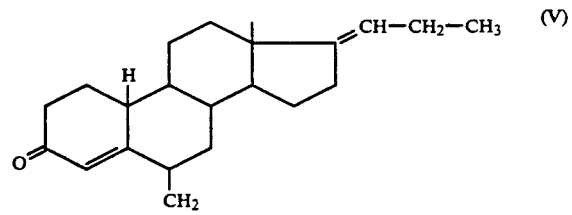

(in the form of a E or Z isomer)
    one isomerizes the latter by reacting it with an isomerizing catalyst, to form a 3-oxo 6-methyl estra 4,6-dienic derivative of formula VI

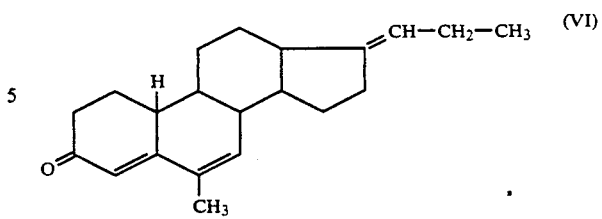

(in the form of a E or Z isomer)
    one submits the latter to a bis-hydroxylation using a bis-hydroxylating reagent made of Osmium Tetroxyde and the hydroperoxyde and a N-oxyde in an inert medium to form the corresponding 17α-hydroxy 20-ketonic derivative having the formula

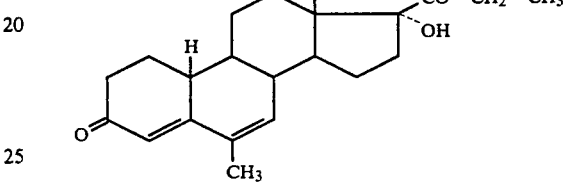

which may be alkylated by means of an alkyl halide in basic medium, or tetrahydropyranylated using dihydropyran in an acidic medium, or acylated using a functional derivative of a carboxylic, or carbonic acid in the presence of an acidic reagent.

The reaction of the compound of formula $II_a$ OR $II_b$ with triarylpropyl phosphium halide or the ylide thereof, mainly leads to the Z isomer in position 17. However the E isomer which is produced only in a limited proportion may be isolated using physical methods and the further steps of this synthesis may well be performed without marked difference either with the Z isomer or with the E isomer.

The process according to this invention may also be defined by the following features which are presently preferred:

1. The reaction of the 17-oxo gonane of formula $II_a$ or $II_b$ with a triaryl propyl phosphonium halide is performed in a basic medium in a polar solvent.
2. The basic reagent is sodium hydride, lithium isopropylamide, potassium terbutylate or sodium amide.
3. The polar solvent is dimethyl sulfoxyde, or hexamethyl phosphorotriamide.
4. The reduction of the compound of formula $III_a$ according to the Birch's method is carried out by reduction in liquid ammonia, followed by a treatment with a strong acid such as hydrochloric acid.
5. The Vilsmeier-Hack's reagent is produced by reaction between phosphorus oxychloride with a tertiary amine-such as dimethylaniline or a disubstituted amide such as dimethyl formamide.
6. The reduction of the 6-formylated compound is performed using an alkali metal aluminohydride or an alkali metal borohydride in a non-reactive solvent such as a cyclic ether or an alkanol.
7. The deshydratation of the 6-hydroxy methylated derivative into a 6-methylenic derivative is carried out by treating it with a strong acid such as hydrochloric acid, perchloric acid or sulphuric acid.
8. The isomerizing reagent is a metal of the family of platinum absorbed on an inert carrier, such as palladium on coal, platinum on coal, or palladium on calcium carbonate.

9. The bis-hydroxylating reaction is performed using Osmium Tetroxyde and a hydroperoxyde of a N-oxyde of tertiary or secondary amide such as the N-oxyde of Trimethylamine, the N-oxyde or Triethylamine or the N-oxyde of Morpholine.

10. The acylation of the 17α-hydroxy derivative is carried out by means of a chloride or an anhydride of an acid in the presence of a strong mineral acid such as hydrochloric acid, or sulphuric acid or a Lewis acid such as Boron trifluoride.

11. Alkylation of the 17α-hydroxy derivative is performed by means of methoxy methanol or dihydropyran in the presence of p.toluene sulphonic acid in an inert solvent.

This invention also includes the pharmaceutical compositions containing as active ingredient at least one compound of general formula I in admixture or conjunction with an inert non-toxic pharmaceutically-acceptable carrier or vehicle.

These pharmaceutical compositions are intended for administration through the parenteral, oral, rectal, permucous, percutaneous or pernasal ways of administration.

For the administration by parenteral way the compounds of general formula I are given in the form of injectible solutions or suspensions packed in ampuls, in multi-dosis flasks or auto-injectible syringes.

For the administration by oral way, the compounds of general formula I are given in the form of coated or uncoated tablets, dragees, soft gelatine capsules, capsules, pills, powders or grandulates.

For the administration by rectal way, the compounds of general formula I are in the form of rectal suppositories or capsules.

For the administration through the permucous way, the compounds of general formula I are formulated as an oily solution as a cream, as a gel or in the form of capsule. It is possible to administrate the compounds of general formula I either through the vaginal mucosa either through the nasal mucosa in the form of a spray or a gel.

For the percutaneous way of administration the compounds of general formula I are formulated as a solution or as a cream in a penetrating solvent such as benzylic alcohol, dimethylsulfoxyde or Azone ®.

These pharmaceutical composition find a therapeutic use for treating the gynecological disorders bound to a luteral insufficiency such as a menstrual dysfunction, dysmenorrhea, premenstrual syndrom and menopausial disturbances.

The usual dosology ranges from 0.05 to 254 mg per unit and the daily dosology ranges from 0.1 to 50 mg in continuous or intermittent administration.

This invention still extends to the intermediate compounds obtained during the synthesis as a mean, to say: the 6-formyl 3-alkoxy 17(20)-propyliden 19-nor estra 3,5-diens (in the form of a E or Z isomer) having the general formula IV The 6-methylene 3-oxo 17(20)-propyliden 19-nor estra 4-en (in the form of a E or Z isomer) having the formula V The 6-methyl 3-oxo 17(20)-propylidene estra 4-6 dien (in the form of an E or Z isomer) having the formula VI The following examples are merely intended to illustrate the invention.

EXAMPLE I 6,21-dimethyl 17α-hydroxy 3,20-dioxo 19-nor pregna 4,6-diene

Step A: 3-alkoxy 21-methyl 19-nor pregna 3,5,17(20)Trien

Using the process disclosed by A. M. Krubiner and co-workers in J. Org. Chem. 33 (1968) 1713 starting from 3-methoxy 17-keto estra 1,3,5(10) trien (IV), they are successively obtained 3-methoxy 21-methyl estra 1,3,5(10) 17(20)tetraen (V) (MP=76° $[\alpha]_D=+59°$) then 3-keto 21-methyl 19nor pregna 4,17(20) diene (VI) obtained after reduction according to the method of Birch-Nelson in the form of a fluid straw-yellowish oil ($[\alpha]_D=+47°$). This compound is converted under the action of triethyl orthoformate in the presence of traces of p.toluene sulphonic acid in an ethanolic medium-into 3-ethoxy 21-methyl 19-nor pregna 3,5,17(20) trien (III).

In the same manner 3-keto 21-methyl 19-nor pregna 4,17(20)diene (VI) is converted into 3-methoxy 21-methyl 19-nor pregna 3,5,17(20)triene (VII) using trimethyl orthoformate in or methanolic medium in the presence of traces of p.toluene sulphonic acid.

The yield amounts to 79% -MP=118° C.,

Step B: 3-ethoxy 6-formyl 21-methyl 19-nor pregna 1,5,17(20)Trien-Isomer Z (VIII)

To 30 g of 3-Ethoxy 21-methyl 19-nor pregna 3,5,17(20)Trien, isomer Z (III) and 300 ml dimethyl formamide it is added a Vilsmeier-Hack's reagent made of 15.5 ml phosphorous oxychloride and 124 ml dimethyl formamide at +5° C. The reaction mixture is kept under stirring for 75 mn–140 ml of an aqueous saturated solution of sodium acetate are added thereto. It appears a crystalline yellow precipitate. After 15 mn standing, the mixture is filtered and washed with water. After filtration and washing, 20.2 g of 3-ethoxy 6-formyl 21-methyl 19-nor pregna 1,5,17(20)Trien (isomer Z) (VIII) are recovered as yellow crystalls.

The yield amounts to 52%. The MP of the pure compound is 99° C. Rotatory power $[\alpha]_D=-21.5°$ (C=1% dioxan).

Step C: 6-methylene 3-oxo 21-methyl 19-nor pregna 4,17(20)diene (isomer Z) (IX)

14.3 g Ethoxy 6-formyl 21-methyl 19-nor pregna 1,5,17(20)Trien (isomer Z) (VIII) and 140 ml methanol are kept under stirring for 80 nm with 960 mg Sodium Borohydride at 0° C. 15 ml of a 2N solution of hydrochloric acid are then slowly added. The mixture is stirred until crystals are obtained. 8.7 g of 6-methylene 3-oxo 21-methyl 19-nor pregna 4,17(20)diene (isomer Z) (IX) are recovered.

The yield amounts to 71%. The melting point is 110°–114° C. The rotation power $[\alpha]_D$ is +218° (C=1% dioxan).

U.V. SPECTRUM: λmax 261 nm ε=10.600.

Step D: 6,21-dimethyl 3-oxo 19-nor pregna 4,6,17(20) trien Z) (X)

3.5 g 6-methylene 3-oxo 21-methyl 19-nor pregna 4,17(20)diene (isomer Z) (IX), 35 g sodium acetate and 1.4 g palladized coal at 5% in 350 ml ethanol; are refluxed for 90 mn. The reaction medium is filtered, extracted with chloroform and the organic phase is washed with water. The organic phases are chromatographied on silica. In the eluates 3.1 g 6,21-dimethyl 3-oxo 19-nor pregna 4,6,17(20)-Trien (isomer Z) (X) are recovered in the form of slightly yellowish oil. The yield is 88%.

The rotatory power is $[\alpha]_D = -31°$ (C=1% dioxan).
U.V. SPECTRUM: $\lambda max = 288$ nm $\epsilon = 22.000$.

Step E: 6,21-dimethyl 17α-hydroxy 3,20-dioxo 19-nor pregna 4,6-diene 2.9 g 6,21-dimethyl 3-oxo 19-nor pregna 4,6,17(20)triene (X) in 29 ml tertbutanol. 0.58 ml of a 2.5% Osmium tetroxyde solution in tertbutanol and 4.06 g of the complex triethylamine N-oxyde hydroperoxyde are stirred for 24 hours at room temperature. 3 g Celite are further added thereto, then 2 g sodium sulfite in solution in water. They are kept under stirring for further 2 hours.

The whole mixture is extracted by toluene then the organic phase is percolated on a bed of silica for chromatography. The eluates are evaporated off and the dry residue is taken in methanol in the hot. After crystallisation 1.66 g 6,21-dimethyl 17α-hydroxy 3,20-dioxo 19-nor pregna 4,6-diene are recovered. The yield is 52%.
MP=204° C.

EXAMPLE II

17α-acetoxy 6,21-dimethyl 3,20-dioxo 19-nor pregna 4,6-diene 1 g 6,21-dimethyl 17α-hydroxy 3,20-dioxo 19-nor pregna 4,6-diene, 10 ml chloroform, 0.8 ml acetic anhydride and 0.15 g p.toluene sulphonic acid are heated to reflux for 50 mn. 2 ml methanol and 0.1 ml concentrated hydrochloric acid are added and, heated to reflux for a further one hour. The reaction mixture is extracted with chloroform. The chloroformic solution is washed with water, then the solution is evaporated off under preduced pressure.

The residue is taken off in methanol for crystallisation. 780 mg of 17α-acetoxy 6,21-dimethyl 3,20-dioxo 19-nor pregna 4,6-diene are recovered as crystals. The yield is 69%.

U.V. SPECTRUM; $\lambda max$ 288 nm $\epsilon = 23.400$.
M.P. =203° C.
Rotatory power: $[\alpha]_D = -34°$ (C=1% dioxan).
RMN SPECTRUM: in CDCl$_3$
0.68 Hz 3H(S) in C$_{18}$
1.05 Hz 3H (t)
J=7 Hz C$_{22}$
1.86 Hz 3H (s) methyl in C$_6$
2.08 Hz 3H (s) CH$_3$CO
5.95 Hz 1H (s) H in C$_7$
6.05 Hz 1H (s) H in C$_6$.

According to the same process, 6.21-dimethyl 17α-propionyloxy 19-nor pregna 4,6-diene has been obtained using propionyl chloride.

Using the same method by means of caproyl chloride 6,21-dimethyl 17α-caproyloxy 19-nor pregna 4,6-diene is obtained.

Using the same method by means of trimethyl acetyl chloride 6,21-dimethyl 17α-trimethyl acetyloxy 19-nor pregna 4,6-diene is obtained.

Using the same method by means of benzoyl chloride, 6,21-dimethyl 17α-benzoyloxy 19-nor pregna 4,6-diene is obtained.

Using the same method by means of mono chloroacetyl chloride, 6,21-dimethyl 17α-chloracetyloxy 19-nor pregna 4,6-diene is obtained.

EXAMPLE III

Pharmacological Study

The binding to the receptors of progesterone as measured in the uterine receptors versus labelled progesterone, shows for the compounds according to this invention, a specific affinity 2.5 times that of progesterone.

EXAMPLE IV

Tablets of 2.5 mg 17α-acetoxy 6,21-dimethyl 3,20-dioxo 19-nor pregna 4,6-diene

| Active Ingredient | 2.5 g |
|---|---|
| Lactose | 110 g |
| Maïs starch | 7,5 g |
| Corn starch | 8,1 g |
| Carboxymethyl starch (sodium salt) | 4,5 g |
| Magnesium stearate | 12,4 g | for 1000 tablets finished at an average weight of 155 g.

What is claimed is:

1. A 6,21-dimethyl 19-nor pregna diene compound having the following formula (I):

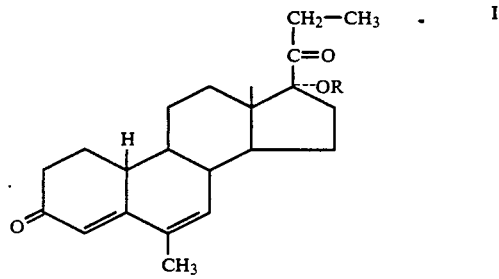

wherein R is a hydrogen, a lower alkyl radical, a methoxy methyl radical, a tetrahydropyranyl radical or the acyl residue of a carbonic carboxylic organic acid having 1–10 carbon atoms.

2. A compound according to claim 1 being 17α-hydroxy 3,20-dioxo 6,21-dimethyl 19-nor pregna 4,6 diene.

3. A compound according to claim 1 being 17α-acetoxy 3,20-dioxo 6,21-dimethyl 19-nor pregna 4,6-diene.

4. A compound according to claim 1 being 17α-tetrahydropyranyloxy 6,21-dimethyl 19-nor pregna 4,6-diene.

5. The pharmaceutical compositions for treatment of dysfunctions relating to the female corpus luteum containing as an active ingredient at least one compound of formula I according to claim 1 in admixture or conjunction with an inert, non-toxic pharmaceutically acceptable carrier or vehicle.

6. A pharmaceutical composition according to claim 5 wherein the carrier or vehicle is one of those suitable for parenteral, oral, rectal, permucous or percutaneous ways of administration.

7. A pharmaceutical composition according to claim 5 wherein the amount of active ingredient ranges from 0.5 to 25.0 mg per unit dosage.

8. A pharmaceutical composition according to claim 7 wherein the carrier or vehicle is one of those suitable for parenteral, oral, rectal, permucous or percutaneous ways of administration.

* * * * *